US008038706B2

(12) United States Patent
Eidenschink et al.

(10) Patent No.: US 8,038,706 B2
(45) Date of Patent: Oct. 18, 2011

(54) CROWN STENT ASSEMBLY (75) Inventors: Tracee Eidenschink, Wayzata, MN (US); Matt Heidner, Maple Grove, MN (US); Michael P. Meyer, Richfield, MN (US); Daniel Gregorich, St. Louis Park, MN (US); Shawn Sorenson, Maple Grove, MN (US); Richard C. Tooley, Crystal, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1624 days.

(21) Appl. No.: 11/221,559

(22) Filed: Sep. 8, 2005

(65) Prior Publication Data

US 2007/0055351 A1 Mar. 8, 2007

(51) Int. Cl.
*A61F 2/06* (2006.01)

(52) U.S. Cl. ................ 623/1.16; 623/1.15; 623/1.35

(58) Field of Classification Search ............. 623/1.15, 623/1.16, 1.2, 1.35, 1.37; 600/36
See application file for complete search history.

(56) References Cited

U.S. PATENT DOCUMENTS

| 4,309,994 A | 1/1982 | Grunwald | 128/214 R |
| 4,769,005 A | 9/1988 | Ginsburg et al. | 604/53 |
| 4,774,949 A | 10/1988 | Fogarty | 128/348.1 |
| 4,896,670 A | 1/1990 | Crittenden | 606/194 |
| 4,905,667 A | 3/1990 | Foerster et al. | 128/4 |
| 4,994,071 A | 2/1991 | MacGregor | 606/194 |
| 5,342,387 A | 8/1994 | Summers | 606/198 |
| 5,387,235 A | 2/1995 | Chuter | 623/1 |
| 5,456,712 A | 10/1995 | Maginot | 623/1 |
| 5,476,471 A | 12/1995 | Shifrin et al. | 606/151 |
| 5,487,730 A | 1/1996 | Marcadis et al. | 604/96 |
| 5,591,228 A | 1/1997 | Edoga | 623/1 |
| 5,607,444 A | 3/1997 | Lam | 606/194 |
| 5,609,605 A | 3/1997 | Marshall et al. | 606/191 |
| 5,609,627 A | 3/1997 | Goicoechea et al. | 623/1 |
| 5,613,980 A | 3/1997 | Chauhan | 606/194 |
| 5,617,878 A | 4/1997 | Taheri | 128/898 |
| 5,632,762 A | 5/1997 | Myler | 606/194 |
| 5,632,763 A | 5/1997 | Glastra | 606/194 |

(Continued)

FOREIGN PATENT DOCUMENTS

CA 2220864 7/1999

(Continued)

OTHER PUBLICATIONS

Chevalier, M.D., Bernard, "Placement of Coronary Stents in Bifurcation Lesions by the "Culotte" Technique," *The American Journal of Cardiology*, vol. 82, pp. 943-949 (Oct. 15, 1998).

(Continued)

*Primary Examiner* — Darwin Erezo
*Assistant Examiner* — Steven Ou
(74) *Attorney, Agent, or Firm* — Vidas, Arrett & Steinkruas (57) ABSTRACT

A stent assembly comprises a proximal stent and a distal stent. Each stent has a tubular body defining a stent lumen and a circumference. A proximal flap extends from the distal end of the proximal stent and a distal flap extends from the proximal end of the distal stent. Each flap defines only a portion of the circumference. In an expanded state the proximal flap and the distal flap form a side branch support having a side branch support lumen. The side branch support lumen is in fluid communication with the stent lumen and has a longitudinal axis different from that of the stent lumen.

20 Claims, 4 Drawing Sheets

U.S. PATENT DOCUMENTS

| | | | | |
|---|---|---|---|---|
| 5,632,772 A | 5/1997 | Alcime et al. ................. 623/1 |
| 5,636,641 A | 6/1997 | Fariabi ........................ 600/585 |
| 5,669,924 A | 9/1997 | Shaknovich ................. 606/108 |
| 5,669,932 A | 9/1997 | Fischell et al. .............. 606/198 |
| 5,676,697 A | 10/1997 | McDonald ..................... 623/1 |
| 5,683,450 A | 11/1997 | Goicoechea et al. .......... 623/1 |
| 5,697,971 A | 12/1997 | Fischell et al. ................. 623/1 |
| 5,707,348 A | 1/1998 | Krogh ........................... 602/41 |
| 5,709,713 A | 1/1998 | Evans et al. .................... 623/1 |
| 5,720,735 A | 2/1998 | Dorros ........................ 604/284 |
| 5,749,825 A | 5/1998 | Fischell et al. ................ 600/3 |
| 5,749,890 A | 5/1998 | Shaknovich ................. 606/198 |
| 5,755,734 A | 5/1998 | Richter et al. ............... 606/194 |
| 5,755,735 A | 5/1998 | Richter et al. ............... 606/194 |
| 5,755,771 A | 5/1998 | Penn et al. ..................... 623/1 |
| 5,755,773 A | 5/1998 | Evans et al. .................... 623/1 |
| 5,755,778 A | 5/1998 | Kleshinski ..................... 623/1 |
| 5,782,906 A | 7/1998 | Marshall et al. .............. 623/1 |
| 5,824,036 A | 10/1998 | Lauterjung ..................... 623/1 |
| 5,824,040 A | 10/1998 | Cox et al. ....................... 623/1 |
| 5,827,320 A | 10/1998 | Richter et al. ............... 606/194 |
| 5,851,464 A | 12/1998 | Davila et al. ................. 264/103 |
| 5,868,777 A | 2/1999 | Lam ............................ 606/194 |
| 5,893,887 A | 4/1999 | Jayaraman ..................... 623/1 |
| 5,906,640 A | 5/1999 | Penn et al. ..................... 623/1 |
| 5,961,548 A | 10/1999 | Shmulewitz ................... 623/1 |
| 5,972,017 A | 10/1999 | Berg et al. ................... 606/198 |
| 6,013,054 A | 1/2000 | Yan ............................... 604/96 |
| 6,013,091 A | 1/2000 | Ley et al. .................... 606/191 |
| 6,017,324 A | 1/2000 | Tu et al. ....................... 604/96 |
| 6,017,363 A | 1/2000 | Hojeibane ..................... 623/1 |
| 6,030,414 A | 2/2000 | Taheri ........................... 623/1 |
| 6,033,434 A | 3/2000 | Borghi .......................... 623/1 |
| 6,033,435 A | 3/2000 | Penn et al. ..................... 623/1 |
| 6,056,775 A | 5/2000 | Borghi et al. .............. 623/1.16 |
| 6,059,824 A | 5/2000 | Taheri ........................... 623/1 |
| 6,068,655 A | 5/2000 | Seguin et al. .................. 623/1 |
| 6,086,611 A | 7/2000 | Duffy et al. .................... 623/1 |
| 6,093,203 A | 7/2000 | Uflacker .................... 612/1.12 |
| 6,096,073 A | 8/2000 | Webster et al. ............ 623/1.16 |
| 6,099,497 A | 8/2000 | Adams et al. ............. 604/96.01 |
| 6,113,579 A | 9/2000 | Eidenschink et al. ........ 604/264 |
| 6,117,117 A | 9/2000 | Mauch ........................ 604/284 |
| 6,117,156 A | 9/2000 | Richter et al. ............... 606/194 |
| 6,129,738 A | 10/2000 | Lashinski et al. ............ 606/194 |
| 6,142,973 A | 11/2000 | Carleton et al. ............... 604/96 |
| 6,143,002 A | 11/2000 | Vietmeier .................... 606/108 |
| 6,159,238 A | 12/2000 | Killion et al. ............... 612/1.11 |
| 6,165,195 A | 12/2000 | Wilson et al. ............... 606/194 |
| 6,168,621 B1 | 1/2001 | Vrba .............................. 623/1.2 |
| 6,183,509 B1 | 2/2001 | Dibie ......................... 623/1.35 |
| 6,203,568 B1 | 3/2001 | Lombardi et al. ........... 623/1.13 |
| 6,210,380 B1 | 4/2001 | Mauch ........................ 604/284 |
| 6,210,429 B1 | 4/2001 | Vardi et al. ................. 623/1.11 |
| 6,210,433 B1 | 4/2001 | Larre .......................... 623/1.15 |
| 6,254,593 B1 | 7/2001 | Wilson ........................ 606/1.11 |
| 6,258,115 B1 | 7/2001 | Dubrul ........................ 606/200 |
| 6,258,116 B1 | 7/2001 | Hojeibane .................. 623/1.16 |
| 6,261,305 B1 | 7/2001 | Marotta et al. .............. 606/200 |
| 6,261,316 B1 | 7/2001 | Shaolian et al. ............ 623/1.11 |
| 6,264,662 B1 | 7/2001 | Lauterjung ................. 606/108 |
| 6,264,682 B1 | 7/2001 | Wilson et al. .............. 623/1.11 |
| 6,264,686 B1 | 7/2001 | Rieu et al. .................. 623/1.16 |
| 6,290,673 B1 | 9/2001 | Shanley ................... 604/102.02 |
| 6,293,968 B1 | 9/2001 | Taheri ......................... 623/1.15 |
| 6,325,826 B1 | 12/2001 | Vardi et al. ................. 623/1.35 |
| 6,334,864 B1 | 1/2002 | Amplatz et al. ............ 606/200 |
| 6,346,089 B1 | 2/2002 | Dibie ........................... 603/1.15 |
| 6,355,060 B1 | 3/2002 | Lenker et al. ............... 623/1.34 |
| 6,361,544 B1 | 3/2002 | Wilson et al. .............. 606/194 |
| 6,361,555 B1 | 3/2002 | Wilson ........................ 623/1.11 |
| 6,383,213 B2 | 5/2002 | Wilson et al. .............. 623/1.11 |
| 6,395,018 B1 | 5/2002 | Castaneda .................. 623/1.13 |
| 6,436,104 B2 | 8/2002 | Hojeibane .................. 606/108 |
| 6,436,134 B2 | 8/2002 | Richter et al. ............. 623/1.15 |
| 6,508,836 B2 | 1/2003 | Wilson et al. .............. 623/1.35 |
| 6,517,558 B2 | 2/2003 | Gittings et al. ............. 606/153 |
| 6,520,988 B1 | 2/2003 | Colombo et al. ........... 623/1.35 |
| 6,540,779 B2 | 4/2003 | Richter et al. .............. 623/1.35 |
| 6,579,309 B1 | 6/2003 | Loos et al. .................. 623/1.16 |
| 6,579,312 B2 | 6/2003 | Wilson et al. .............. 623/1.35 |
| 6,582,394 B1 | 6/2003 | Reiss et al. ............... 604/96.01 |
| 6,596,020 B2 | 7/2003 | Vardi et al. ................. 623/1.11 |
| 6,599,316 B2 | 7/2003 | Vardi et al. ................. 623/1.15 |
| 6,645,242 B1 | 11/2003 | Quinn ......................... 623/1.16 |
| 6,689,156 B1 | 2/2004 | Davidson et al. .......... 623/1.11 |
| 6,692,483 B2 | 2/2004 | Vardi et al. ................. 604/529 |
| 6,695,877 B2 | 2/2004 | Brucker et al. ............. 623/1.16 |
| 6,706,062 B2 | 3/2004 | Vardi et al. ................. 623/1.15 |
| 6,749,628 B1 | 6/2004 | Callol et al. ................ 623/1.15 |
| 6,776,793 B2 | 8/2004 | Brown et al. ............... 623/1.15 |
| 6,811,566 B1 | 11/2004 | Penn et al. .................. 623/1.15 |
| 6,835,203 B1 | 12/2004 | Vardi et al. ................. 623/1.34 |
| 6,858,038 B2 | 2/2005 | Heuser ........................ 623/1.35 |
| 6,884,258 B2 | 4/2005 | Vardi et al. ................. 623/1.11 |
| 6,896,699 B2 | 5/2005 | Wilson et al. .............. 623/1.35 |
| 6,932,837 B2 | 8/2005 | Amplatz et al. ............ 623/1.15 |
| 6,945,995 B2 * | 9/2005 | Nicholas ..................... 623/1.34 |
| 6,955,687 B2 | 10/2005 | Richter et al. .............. 623/1.35 |
| 6,955,688 B2 | 10/2005 | Wilson et al. .............. 623/1.35 |
| 6,962,602 B2 | 11/2005 | Vardi et al. ................. 623/1.11 |
| 7,018,400 B2 | 3/2006 | Lashinski et al. ........... 623/1.11 |
| 7,056,323 B2 | 6/2006 | Mareiro et al. ............. 606/108 |
| 7,060,091 B2 | 6/2006 | Killion et al. .............. 623/1.15 |
| 2001/0003161 A1 | 6/2001 | Vardi et al. ................. 623/1.11 |
| 2001/0004706 A1 | 6/2001 | Hojeibane .................. 623/1.11 |
| 2001/0004707 A1 | 6/2001 | Dereurne et al. ........... 623/1.16 |
| 2001/0012927 A1 | 8/2001 | Mauch ........................ 604/284 |
| 2001/0016766 A1 | 8/2001 | Vardi et al. ................. 623/1.11 |
| 2001/0016767 A1 | 8/2001 | Wilson et al. .............. 623/1.11 |
| 2001/0016768 A1 | 8/2001 | Wilson et al. .............. 623/1.11 |
| 2001/0025195 A1 | 9/2001 | Shaolian et al. ............ 623/1.13 |
| 2001/0027291 A1 | 10/2001 | Shanley ...................... 604/104 |
| 2001/0027338 A1 | 10/2001 | Greenberg .................. 623/1.13 |
| 2001/0029396 A1 | 10/2001 | Wilson et al. .............. 623/1.11 |
| 2001/0037116 A1 | 11/2001 | Wilson et al. .............. 606/108 |
| 2001/0037138 A1 | 11/2001 | Wilson et al. .............. 623/1.11 |
| 2001/0039448 A1 | 11/2001 | Dibie .......................... 623/1.16 |
| 2001/0049548 A1 * | 12/2001 | Vardi et al. ................. 623/1.11 |
| 2001/0049552 A1 | 12/2001 | Richter et al. .............. 623/1.15 |
| 2001/0056297 A1 | 12/2001 | Hojeibane .................. 623/1.16 |
| 2002/0013618 A1 | 1/2002 | Marotta et al. ............. 623/1.15 |
| 2002/0013619 A1 | 1/2002 | Shanley ...................... 623/1.15 |
| 2002/0022874 A1 | 2/2002 | Wilson ........................ 623/1.11 |
| 2002/0026232 A1 | 2/2002 | Marotta et al. ............. 623/1.16 |
| 2002/0035392 A1 | 3/2002 | Wilson ........................ 623/1.11 |
| 2002/0042650 A1 | 4/2002 | Vardi et al. ................. 623/1.35 |
| 2002/0052648 A1 | 5/2002 | McGuckin, Jr. et al. ... 623/1.35 |
| 2002/0072790 A1 | 6/2002 | McGuckin, Jr. et al. ... 623/1.12 |
| 2002/0111675 A1 | 8/2002 | Wilson ........................ 623/1.35 |
| 2002/0151953 A1 * | 10/2002 | Chobotov et al. .......... 623/1.11 |
| 2002/0156516 A1 | 10/2002 | Vardi et al. ................. 623/1.11 |
| 2002/0156517 A1 | 10/2002 | Perouse ...................... 623/1.11 |
| 2002/0165604 A1 | 11/2002 | Shanley ...................... 623/1.15 |
| 2002/0173835 A1 | 11/2002 | Bourang et al. ............ 623/1.11 |
| 2002/0173839 A1 * | 11/2002 | Leopold et al. ............ 623/1.15 |
| 2002/0173840 A1 | 11/2002 | Brucker et al. ............. 623/1.16 |
| 2002/0183763 A1 | 12/2002 | Callol et al. ................ 606/108 |
| 2002/0193872 A1 | 12/2002 | Trout, III et al. ........... 623/1.34 |
| 2002/0193873 A1 | 12/2002 | Brucker et al. ............. 623/1.35 |
| 2003/0009209 A1 | 1/2003 | Hojeibane .................. 623/1.11 |
| 2003/0028233 A1 | 2/2003 | Vardi et al. ................. 623/1.11 |
| 2003/0045926 A1 * | 3/2003 | Pinchasik ................... 623/1.16 |
| 2003/0050688 A1 | 3/2003 | Fischell et al. ............. 623/1.15 |
| 2003/0055378 A1 | 3/2003 | Wang et al. ............. 604/103.07 |
| 2003/0055483 A1 | 3/2003 | Gumm ........................ 623/1.11 |
| 2003/0074047 A1 | 4/2003 | Richter ....................... 623/1.11 |
| 2003/0093109 A1 | 5/2003 | Mauch ........................ 606/194 |
| 2003/0097169 A1 | 5/2003 | Brucker ...................... 623/1.11 |
| 2003/0114912 A1 | 6/2003 | Sequin et al. .............. 623/1.11 |
| 2003/0125791 A1 | 7/2003 | Sequin et al. .............. 623/1.11 |
| 2003/0125802 A1 | 7/2003 | Callol et al. ................ 623/1.35 |
| 2003/0135259 A1 | 7/2003 | Simso ......................... 623/1.12 |
| 2003/0181923 A1 | 9/2003 | Vardi .......................... 606/108 |
| 2003/0195606 A1 | 10/2003 | Davidson et al. .......... 623/1.11 |
| 2003/0204245 A1 * | 10/2003 | Brightbill ................... 623/1.16 |
| 2004/0006381 A1 | 1/2004 | Sequin et al. .............. 623/1.12 |

| | | | |
|---|---|---|---|
| 2004/0015227 A1 | 1/2004 | Vardi et al. ............. 623/1.16 |
| 2004/0044396 A1 | 3/2004 | Clerc et al. ............. 623/1.13 |
| 2004/0044398 A1* | 3/2004 | Nicholas ................ 623/1.16 |
| 2004/0059406 A1 | 3/2004 | Cully et al. ............. 623/1.11 |
| 2004/0088007 A1 | 5/2004 | Eidenschink ............. 607/1 |
| 2004/0093067 A1* | 5/2004 | Israel .................... 623/1.15 |
| 2004/0117003 A1 | 6/2004 | Ouriel et al. ............ 623/1.35 |
| 2004/0133268 A1 | 7/2004 | Davidson et al. ......... 623/1.35 |
| 2004/0138732 A1 | 7/2004 | Suhr et al. .............. 623/1.11 |
| 2004/0138737 A1 | 7/2004 | Davidson et al. ......... 623/1.35 |
| 2004/0148006 A1 | 7/2004 | Davidson et al. ......... 623/1.11 |
| 2004/0172121 A1 | 9/2004 | Eidenschink et al. ...... 623/1.11 |
| 2004/0186560 A1 | 9/2004 | Alt ...................... 623/1.35 |
| 2004/0215327 A1* | 10/2004 | Doig et al. .............. 623/1.16 |
| 2004/0225345 A1 | 11/2004 | Fischell et al. ........... 623/1.11 |
| 2004/0267352 A1 | 12/2004 | Davidson et al. ......... 623/1.15 |
| 2005/0004656 A1 | 1/2005 | Das ...................... 623/1.16 |
| 2005/0010278 A1 | 1/2005 | Vardi et al. ............. 623/1.35 |
| 2005/0015108 A1 | 1/2005 | Williams et al. .......... 606/194 |
| 2005/0015135 A1 | 1/2005 | Shanley ................. 623/1.11 |
| 2005/0021128 A1* | 1/2005 | Nakahama et al. ......... 623/1.15 |
| 2005/0060027 A1 | 3/2005 | Khenansho et al. ........ 623/1.35 |
| 2005/0096726 A1 | 5/2005 | Sequin et al. ............ 623/1.12 |
| 2005/0102021 A1 | 5/2005 | Osborne ................. 623/1.13 |
| 2005/0102023 A1 | 5/2005 | Yadin et al. ............. 623/1.15 |
| 2005/0119731 A1 | 6/2005 | Brucker et al. ........... 623/1.35 |
| 2005/0125076 A1 | 6/2005 | Ginn .................... 623/23.65 |
| 2005/0131526 A1 | 6/2005 | Wong .................... 623/1.15 |
| 2005/0149161 A1 | 7/2005 | Eidenschink et al. ...... 623/1.11 |
| 2005/0154442 A1 | 7/2005 | Eidenschink et al. ...... 623/1.11 |
| 2005/0154444 A1 | 7/2005 | Quadri .................. 623/1.13 |
| 2005/0183259 A1 | 8/2005 | Eidenschink et al. ...... 29/508 |
| 2005/0209673 A1 | 9/2005 | Shaked .................. 623/1.11 |
| 2005/0228483 A1 | 10/2005 | Kaplan et al. ............ 623/1.15 |
| 2006/0036315 A1 | 2/2006 | Yadin et al. ............. 623/1.35 |
| 2006/0041303 A1 | 2/2006 | Israel .................... 623/1.11 |
| 2006/0079956 A1 | 4/2006 | Eigler et al. ............. 623/1.35 |
| 2006/0173528 A1 | 8/2006 | Feld et al. ............... 623/1.15 |
| 2006/0287712 A1 | 12/2006 | Eidenschink |
| 2007/0073376 A1 | 3/2007 | Krolik et al. ............. 623/1.11 |

FOREIGN PATENT DOCUMENTS

| | | |
|---|---|---|
| DE | 9014845 | 2/1991 |
| DE | 29701758 | 3/1997 |
| DE | 29701883 | 5/1997 |
| EP | 0479730 | 10/1991 |
| EP | 0751752 | 1/1997 |
| EP | 0783873 | 7/1997 |
| EP | 0804907 | 11/1997 |
| EP | 0479557 | 7/1998 |
| EP | 0876805 | 11/1998 |
| EP | 0880949 | 12/1998 |
| EP | 0891751 | 1/1999 |
| EP | 0895759 | 2/1999 |
| EP | 0904745 | 3/1999 |
| EP | 0937442 | 8/1999 |
| EP | 0347023 | 12/1999 |
| EP | 1031328 | 8/2000 |
| EP | 1031329 | 8/2000 |
| EP | 0883384 | 12/2000 |
| EP | 0862392 | 8/2001 |
| EP | 0808140 | 12/2001 |
| EP | 0884028 | 2/2002 |
| EP | 1190685 | 3/2002 |
| EP | 0897700 | 7/2002 |
| EP | 0684022 | 2/2004 |
| EP | 1 470 797 A2 | 10/2004 |
| EP | 1157674 | 7/2005 |
| EP | 1031330 | 11/2005 |
| EP | 1070513 | 6/2006 |
| FR | 2678508 | 1/1993 |
| FR | 2740346 | 10/1995 |
| FR | 2756173 | 11/1996 |
| GB | 2337002 | 5/1998 |
| WO | 88/06026 | 8/1988 |
| WO | 95/21592 | 8/1995 |
| WO | 96/29955 | 10/1996 |
| WO | 96/34580 | 11/1996 |
| WO | 96/41592 | 12/1996 |
| WO | 97/07752 | 3/1997 |
| WO | 97/15346 | 5/1997 |
| WO | 97/16217 | 5/1997 |
| WO | 97/26936 | 7/1997 |
| WO | 97/41803 | 11/1997 |
| WO | 97/45073 | 12/1997 |
| WO | 97/46174 | 12/1997 |
| WO | 98/19628 | 5/1998 |
| WO | 98/36709 | 8/1998 |
| WO | 98/37833 | 9/1998 |
| WO | 98/47447 | 10/1998 |
| WO | 98/48879 | 11/1998 |
| WO | 99/03426 | 1/1999 |
| WO | 99/04726 | 2/1999 |
| WO | 99/15103 | 4/1999 |
| WO | 99/15109 | 4/1999 |
| WO | 99/24104 | 5/1999 |
| WO | 99/34749 | 7/1999 |
| WO | 99/36002 | 7/1999 |
| WO | 99/36015 | 7/1999 |
| WO | 99/44539 | 9/1999 |
| WO | 99/56661 | 11/1999 |
| WO | 99/65419 | 12/1999 |
| WO | 00/07523 | 2/2000 |
| WO | 00/10489 | 3/2000 |
| WO | 00/16719 | 3/2000 |
| WO | 00/27307 | 5/2000 |
| WO | 00/27463 | 5/2000 |
| WO | 00/28922 | 5/2000 |
| WO | 01/45594 | 6/2000 |
| WO | 00/44307 | 8/2000 |
| WO | 00/44309 | 8/2000 |
| WO | 00/47134 | 8/2000 |
| WO | 00/48531 | 8/2000 |
| WO | 00/49951 | 8/2000 |
| WO | 00/51523 | 9/2000 |
| WO | 00/57813 | 10/2000 |
| WO | 00/67673 | 11/2000 |
| WO | 00/71054 | 11/2000 |
| WO | 00/71055 | 11/2000 |
| WO | 00/74595 | 12/2000 |
| WO | 01/21095 | 3/2001 |
| WO | 01/21109 | 3/2001 |
| WO | 01/21244 | 3/2001 |
| WO | 01/35715 | 5/2001 |
| WO | 01/35863 | 5/2001 |
| WO | 01/39697 | 6/2001 |
| WO | 01/39699 | 6/2001 |
| WO | 01/41677 | 6/2001 |
| WO | 01/43665 | 6/2001 |
| WO | 01/43809 | 6/2001 |
| WO | 01/45785 | 6/2001 |
| WO | 01/49342 | 7/2001 |
| WO | 01/54621 | 8/2001 |
| WO | 01/54622 | 8/2001 |
| WO | 01/58385 | 8/2001 |
| WO | 01/60284 | 8/2001 |
| WO | 01/70294 | 9/2001 |
| WO | 01/70299 | 9/2001 |
| WO | 01/74273 | 10/2001 |
| WO | 01/89409 | 11/2001 |
| WO | 02/00138 | 1/2002 |
| WO | 02/053066 | 7/2002 |
| WO | 02/068012 | 9/2002 |
| WO | 03/007842 | 1/2003 |
| WO | 03/055414 | 7/2003 |
| WO | 03/063924 | 8/2003 |
| WO | 2004/026174 | 4/2004 |
| WO | 2004/026180 | 4/2004 |
| WO | 2005/009295 | 2/2005 |
| WO | 2005/014077 | 2/2005 |
| WO | 2006/028925 | 3/2006 |

OTHER PUBLICATIONS

Nakamura M.D., Shigeru, "Techniques for Palmaz-Schatz Stent Deployment in Lesions with a Large Side Branch," *Catheterization and Cardiovascular Diagnosis*, vol. 34, pp. 353-361 (1995).

Caputo, Ronald P., "Stent Jail: A Minimum-Security Prison," *The American Journal of Cardiology*, vol. 77, pp. 1226-1230 (Jun. 1, 1996).

Colombo, M.D., Antonio, ""Kissing" Stent for Bifurcational Coronary Lesion," *Catheterization and Cardiovascular Diagnosis*, vol. 30, pp. 327-330 (Dec. 1993).

Carrie, M.D., Didier, "T"-Shaped Stent Placement: A Technique for the Treatment of Dissected Bifurcation Lesions, *Catheterization and Cardiovascular Diagnosis*, vol. 37, pp. 311-313 (Mar. 1996).

Katoh, M.D., Osamu, "New Double Wire Technique to Stent Ostial Lesions," *Catheterization and Cardiovascular Diagnosis*, vol. 40, pp. 400-402 (Apr. 1997).

Lewis, M.D., Bruce E., "Acute procedural results in the treatment of 30 coronary artery bifurcation lesions with a double-wire atherectomy technique for side-branch protection," *American Heart Journal*, vol. 127:6, pp. 1600-1607 (Jun. 1994).

Yamashita, M.D.,PhD., Takehiro, "Bifurcation Lesions: Two Stents Versus One Stent—Immediate and Follow-up Results," *Journal of the American College of Cardiology*, vol. 35:5, pp. 1145-1151 (Apr. 2000).

Satler, M.D., Lowell F., "Bifurcation Disease: To Treat or Not to Treat," *Catheterization and Cardiovascular Interventions*, vol. 50, pp. 411-412 (2000).

U.S. Appl. No. 09/663,111, filed Sep. 15, 2000, Davidson et al.

* cited by examiner

CROWN STENT ASSEMBLY

CROSS-REFERENCE TO RELATED APPLICATIONS

Not Applicable

STATEMENT REGARDING FEDERALLY SPONSORED RESEARCH

Not Applicable

BACKGROUND OF THE INVENTION

1. Field of the Invention

In some embodiments this invention relates to implantable medical devices, their manufacture, and methods of use. Some embodiments are directed to delivery systems, such as catheter systems of all types, which are utilized in the delivery of such devices.

2. Description of the Related Art

A stent is a medical device introduced to a body lumen and is well known in the art. Typically, a stent is implanted in a blood vessel at the site of a stenosis or aneurysm endoluminally, i.e. by so-called "minimally invasive techniques" in which the stent in a radially reduced configuration, optionally restrained in a radially compressed configuration by a sheath and/or catheter, is delivered by a stent delivery system or "introducer" to the site where it is required. The introducer may enter the body from an access location outside the body, such as through the patient's skin, or by a "cut down" technique in which the entry blood vessel is exposed by minor surgical means.

Stents, grafts, stent-grafts, vena cava filters, expandable frameworks, and similar implantable medical devices, collectively referred to hereinafter as stents, are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, fallopian tubes, coronary vessels, secondary vessels, etc. Stents may be used to reinforce body vessels and to prevent restenosis following angioplasty in the vascular system. They may be self-expanding, expanded by an internal radial force, such as when mounted on a balloon, or a combination of self-expanding and balloon expandable (hybrid expandable).

Stents may be created by methods including cutting or etching a design from a tubular stock, from a flat sheet which is cut or etched and which is subsequently rolled or from one or more interwoven wires or braids.

Within the vasculature it is not uncommon for stenoses to form at a vessel bifurcation. A bifurcation is an area of the vasculature or other portion of the body where a first (or parent) vessel is bifurcated into two or more branch vessels. Where a stenotic lesion or lesions form at such a bifurcation, the lesion(s) may affect only one of the vessels (i.e., either of the branch vessels or the parent vessel) two of the vessels, or all three vessels.

Many prior art stents however are not wholly satisfactory for use where the site of desired application of the stent is juxtaposed or extends across a bifurcation in an artery or vein such, for example, as the bifurcation in the mammalian aortic artery into the common iliac arteries.

There remains a need for innovative bifurcated stents which may be deployed using a single balloon for the main section and an alternate mechanism for the side branch support. There also remains a need for bifurcated stents with innovative designs in the region of the bifurcation to provide adequate coverage of the carina. The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

In at least one embodiment, the invention is directed to a stent comprising a proximal stent and a distal stent. Each stent has a tubular body defining a stent lumen, a longitudinal axis and a circumference. A proximal flap extends from the distal end of the proximal stent and a distal flap extends from the proximal end of the distal stent.

In at least one embodiment, each flap is characterized as a non-tubular or substantially planar structure which defines only a portion of the circumference of the otherwise tubular body of a given stent.

In at least one embodiment, the flaps comprise a cross-sectional length equal to about half the circumference of the tubular body. In some embodiments the cross-sectional length is greater or less than about half the circumference of the tubular body.

The stents are expandable from a reduced diameter configuration in an unexpanded or pre-deployed state to a greater diameter in an expanded or deployed state. When the stents are properly positioned at a bifurcation junction of two vessels and are expanded to their expanded states, the proximal flap and the distal flap will extend into the secondary or side branch vessel of the bifurcation to effectively form a side branch support structure by way of their adjacency to one another. This side branch support will define a side branch support lumen which is in fluid communication with the common lumen(s) defined by the tubular bodies of the adjacent stents.

The "expanded state" of the flaps, refers to the positional state of the flaps wherein the flaps each extend obliquely from the tubular body of the stent segment and form the side branch support which, in at least one embodiment, covers the contralateral wall and carina, of the ostium region, of the secondary vessel, of the bifurcation.

In at least one embodiment, the tubular bodies are positioned with the ends which include the flaps immediately adjacent one another.

In at least one embodiment, in the expanded state the tubular bodies are engaged to one another.

In at least one embodiment, the proximal stent and the distal stent are welded to one another.

In at least one embodiment, the flaps of the proximal stent segment and the distal stent segment overlap one another.

In at least one embodiment, the flaps of the proximal stent segment and the distal stent segment nest within each other.

In at least one embodiment, the stent assembly is constructed at least partially from a self-expanding material.

In at least one embodiment, the stent assembly is balloon expandable.

In at least one embodiment, the flaps are constructed of self-expanding material. In at least one embodiment, the flaps self-expand to form the side branch support lumen.

In at least one embodiment, at least a portion of the stent assembly is constructed and arranged to carry a therapeutic agent. In at least one embodiment, the therapeutic agent is a coating on the stent assembly. In at least one embodiment, at least one of the flaps contains a different dosing of therapeutic agent than the tubular body from which it extends.

In at least one embodiment, the side branch support lumen is substantially oval-shaped.

In at least one embodiment, the side branch support lumen is substantially polygonal.

In at least one embodiment, the invention is directed to a delivery system for delivering a stent assembly to a vessel bifurcation comprising a catheter and a proximal stent and a distal stent mounted thereon. The stents comprise an assembly wherein, in the unexpanded state the stent assembly can be disposed about the stent retaining region of the catheter shaft. The stent assembly has a tubular body which defines a primary lumen therethrough. In at least one embodiment, flaps extend from both the proximal stent and the distal stent. Each flap comprises a non-tubular body having a substantially planar structure. In at least one embodiment, in the expanded state the flaps form a side branch support having a side branch support lumen which is in fluid communication with the primary lumen.

In at least one embodiment, the delivery system also has a side branch support guide housing. The support guide housing has a tubular member which defines a secondary guidewire lumen therethrough. In at least one embodiment, the side branch support guide housing can be positioned adjacent to the stent retaining region of the catheter shaft. In at least one embodiment, a first portion of the guide housing can extend within the primary lumen defined by the proximal stent and exit the primary lumen through the side branch support lumen.

In at least one embodiment, in the unexpanded state one flap overlays the other.

In at least one embodiment, in the expanded state the proximal flap and the distal flap do not contact one another.

In at least one embodiment, the stent assembly can be assembled by providing a proximal stent having a flap and a distal stent having a flap and moving the proximal stent and the distal stent together such that the flaps form a side branch support.

In at least one embodiment, the proximal stent and the distal stent can be moved together while both are disposed about a catheter.

In at least one embodiment, a method of delivering a stent to a bifurcation comprises the steps of a) advancing any of the stent assemblies above disposed about a catheter along two guidewires and b) deploying the stent at the bifurcation site.

In at least one embodiment, a method of delivering a stent to a bifurcation comprises the steps of a) advancing any of the stent assemblies above disposed about a catheter along two guidewires, the catheter having a catheter shaft and catheter balloon, the stent assembly disposed about the catheter balloon and b) deploying the stent assembly at the bifurcation site by expanding the catheter balloon. In at least one embodiment, expansion of the catheter balloon acts on the stent assembly to expand the stent assembly such that the stent assembly expands to an expanded state.

These and other embodiments which characterize the invention are pointed out with particularity in the claims annexed hereto and forming a part hereof. However, for further understanding of the invention, its advantages and objectives obtained by its use, reference should be made to the drawings which form a further part hereof and the accompanying descriptive matter, in which there is illustrated and described an embodiments of the invention.

BRIEF DESCRIPTION OF THE SEVERAL VIEWS OF THE DRAWING(S)

A detailed description of the invention is hereafter described with specific reference being made to the drawings.

DETAILED DESCRIPTION OF THE INVENTION

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Figure 1:
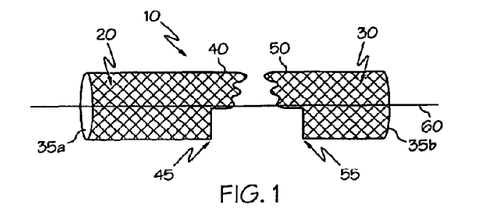
FIG. 1 is a side view of the proximal and distal stents in an unexpanded state.
Figure 2:
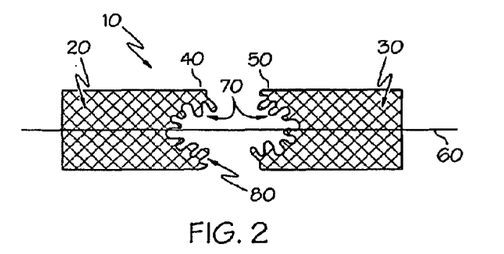
FIG. 2 is a top view of the proximal and distal stents.

In FIG. 1 the proximal stent 20 and the distal stent 30 of stent assembly 10 is shown. Proximal stent 20 defines a proximal stent lumen 35a and distal stent 30 defines a distal stent lumen 35b. The stent assembly 10 is in an unexpanded state. The proximal flap 40 extends from the distal end 45 of proximal stent 20 and the distal flap 50 extends from the proximal end 55 of distal stent 30. The flaps 40 and 50 extend toward one another and in some embodiments are partially disposed about the longitudinal axis 60 at a radial distance substantially the same as the other portions of the stent segment from which it extends. In some embodiments the stent assembly 10 defines spaces 70 in the flaps 40 and 50 as shown in FIG. 2. The spaces 70 may provide easier passage of a guidewire or for insertion of an expansion balloon into the side branch support. In some embodiments flaps 40 and 50 have finger portions 80 that extend into the space 70. The space 70 may be irregularly shaped as shown. In some embodiments the space 70 may be circular, oval, or otherwise shaped. In some embodiments the space may be in the shape of a polygon.

The inventive stents may be created by methods including cutting or etching a design from a tubular stock, from a flat sheet which is cut or etched and which is subsequently rolled or from one or more interwoven wires or braids. Any other suitable technique which is known in the art or which is subsequently developed may also be used to manufacture the inventive stents disclosed herein.

Figure 3:
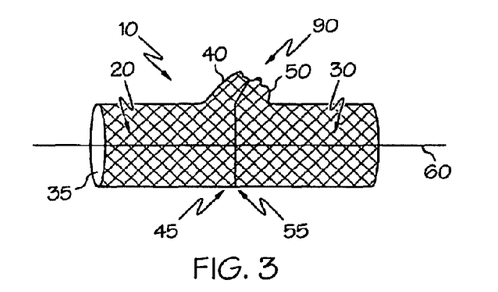
FIG. 3 is a side view of the proximal and distal stents in an expanded state.

In FIG. 3 the stent assembly 10 is in an expanded state. In an expanded state the proximal and distal flaps form a side branch support 90 which extends obliquely from the tubular body portion of the proximal and distal stents 20,30. The proximal flap 40 and the distal flap 50 as shown extend distally at oblique angles in relation to the longitudinal axis 60. In some instances the distal flap 50 in the expanded state extends obliquely in a proximal direction. The sizes of the flaps and the size ratios between the flaps may vary.

In some embodiments the dimensions of the flaps 40 and 50 are the same, while in others they are different. For example, the proximal flap may be longer than the distal flap or vice versa. In some embodiments the arcuate length (width) and/or longitudinal length of one flap may be greater than the other flap. In some embodiment the distal flap 40 is larger than the proximal flap 50. The distal flap 40 in some embodiments is longer than the distal stent 30. In the expanded state the distal end 45 of proximal stent 20 and the proximal end 55 of distal stent 30 are adjacent one another. In some embodiments, the stent segments are in contact with one another. In some embodiments there is a gap between the distal end 45 and the proximal end 55 in the expanded state. In an expanded state the proximal stent lumen and the distal stent lumen form stent lumen 35.

Figure 4:
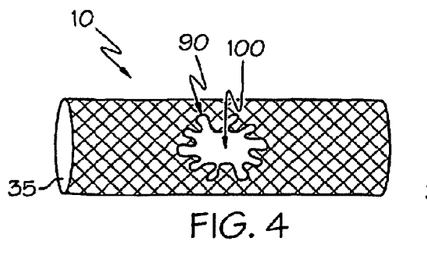
FIG. 4 is a top view of the proximal and distal stents in an expanded state.

As illustrated in FIG. 4, in an expanded state, the assembled stent assembly 10 has a side branch support lumen 100 in fluid communication with the stent lumen 35. As shown here the proximal and distal flaps form a side branch support lumen 100 that is surrounded by the flaps 40 and 50. In some embodiments the flaps 40 and 50 define a space between them, in an expanded state, such that the side branch support lumen is not fully surrounded by the flaps. If desired, the flaps may be constructed to cover the contra lateral wall and carina of the side branch vessel but leave other portions of the ostium region uncovered.

Figure 4A:
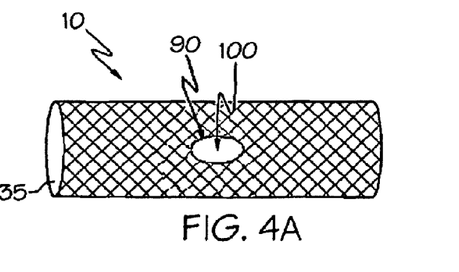
FIG. 4A is a top view of the proximal and distal stents in an expanded state in an alternative embodiment.

As depicted in FIG. 4A, the assembled stent assembly 10, shown in an expanded state, has a substantially oval-shaped side branch support lumen 100 in fluid communication with the stent lumen 35.

Figure 5:
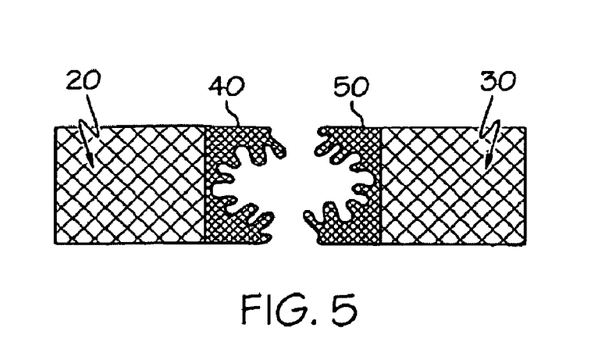
FIG. 5 is a top view of the proximal and distal stents identifying a therapeutic agent.

In some embodiments the at least a portion of the stent is configured to include one or more mechanisms for the delivery of a therapeutic agent. Often the agent will be in the form of a coating or other layer (or layers) of material placed on a surface region of the stent, which is adapted to be released at the site of the stent's implantation or areas adjacent thereto. The therapeutic agent can be applied in a variety of ways and can include therapeutic agent being applied in some locations more than others. In at least one embodiment as shown in FIG. 5, the flaps 40,50 have more therapeutic agent than does the rest of proximal stent 20 and the rest of distal stent 30. In at least one embodiment, one of the flaps has more therapeutic agent than the other flap. In some embodiments, the flaps 40,50 can have less therapeutic agent than at least one of the stents 20,30 excluding the flap portion. In at least one embodiment one flap has more therapeutic agent than does the rest of the stent from which it extends and the other stent and flap. It should be noted that in some instances some portions of the stent assembly will not have any therapeutic agent and that in some embodiments the therapeutic agent will be evenly distributed throughout the stent assembly.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate.

Figure 6:
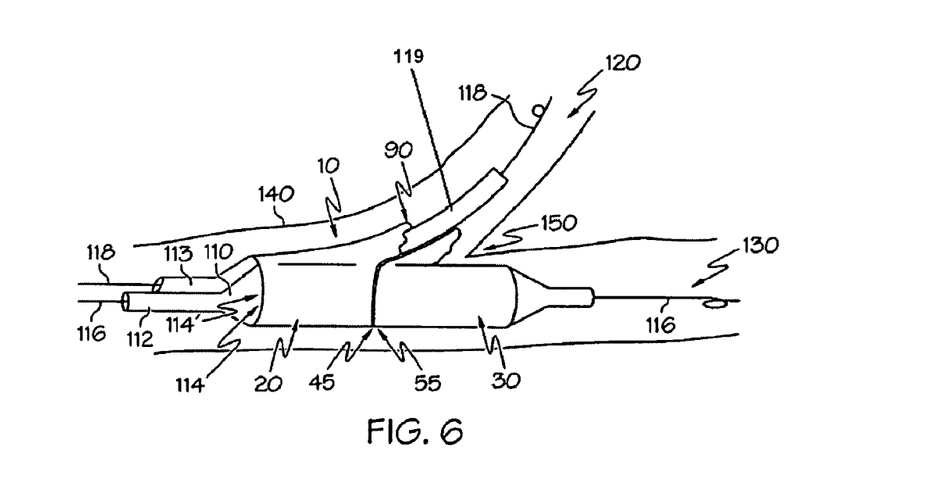
FIG. 6 is a side view of the proximal and distal stents.

The stent assembly may be assembled on or off a catheter. FIG. 6 illustrates a proximal stent 20 and a distal stent 30 assembled on a catheter 110. The proximal stent and distal stent may both be disposed about a catheter 110 and situated in relationship to one another as in FIG. 1 such that the flaps 50 and 40 extend toward one another. Then one or both of the segments 20 and 30 may be moved such that the distal end 45 of proximal segments 20 and the proximal end 55 of distal segment 30 are adjacent one another as shown in FIG. 6.

FIG. 6 also illustrates a delivery system including a catheter 110 having a catheter shaft 112, a secondary guidewire housing 113, a stent retaining region 114, and a side branch support guide housing 119 at a bifurcation site. Proximal stent 20 and distal stent 30 are disposed about stent retaining region 114 and adjacent one another. The stent assembly 10 is advanced to the bifurcation site along primary guidewire 116 and secondary guidewire 118. As seen in FIG. 6, the flaps cover a portion of the contra-lateral wall 140 and the carina 150 of the side branch vessel, while leaving other portions of the ostium region uncovered.

In some embodiments, the guidewires 116 and 118 are inserted into the body to the bifurcation site before the catheter 110 and stent assembly 10 are mounted on the guidewires. The primary guidewire 116 is advanced through the primary vessel lumen 130 to beyond the bifurcation site, and the secondary guidewire 118 is advanced through the primary vessel lumen 130 and at the bifurcation site is advanced into secondary vessel lumen 120. In at least one embodiment, once the primary guidewire 116 is in place within the primary vessel lumen 130 and the secondary guidewire is positioned to extend into the secondary vessel lumen 120 such as in the manner shown in FIG. 6, the catheter 110, with the stent assembly 10, is advanced along both wires simultaneously.

In the embodiment shown in FIG. 6, the secondary guidewire housing 113 extends through the lumen of proximal stent 20 and exits the stent 20 through the side branch support lumen 100 of the side branch support 90. This configuration allows the secondary guidewire housing 113 to provide a torquing and/or rotational effect on the catheter 110 as it is advanced toward the bifurcation along both guidewires. As a result the side branch support 90 will be rotated into alignment with the secondary vessel lumen 120.

Once the system is aligned in the manner shown in FIG. 6, the stent assembly 10 is expanded and deployed.

In some embodiments the stent retaining region 114 comprises a balloon 114'. By expanding the balloon 114' from a reduced diameter to a greater, expanded diameter the balloon 114' will exert expansion and/or deployment forces upon the assembly 10. The expansion forces exerted on the assembly are sufficient to expand the assembly to its deployed state within the vessel bifurcation. Subsequent to the expansion of the assembly 10, the catheter is removed from the vessel lumens 120 and 130, and the assembly 10 remains in place to support the bifurcation. In some embodiments additional radial force within the side branch support lumen may be used to expand side branch support 90.

The stent assembly 10 may also have self-expanding portions. In some embodiments the entire stent assembly 10 is made of self-expanding material; in some embodiments the entire stent assembly 10 is made of non-self-expanding material. In some embodiments, the tubular body portions are made of non-self-expanding material and the side branch support is made of self-expanding material. In some embodiments, the tubular body portions are made of self-expanding material and the side branch support is made of non-self-expanding material.

Figure 7:
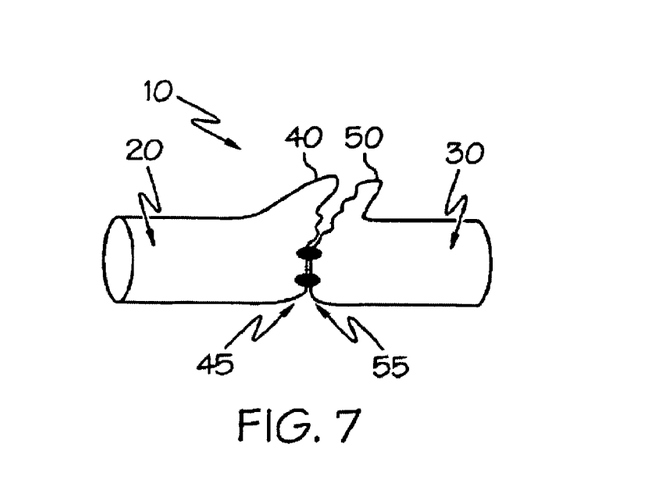
FIG. 7 is a side view of the proximal and distal stents.

The stent assembly 10 may be assembled off the catheter. The proximal stent 20 and the distal stent 30 may be assembled such that the distal end 45 of proximal stent 20 and the proximal end 55 of distal stent 30 are adjacent one another as illustrated in FIG. 7. The ends may also be affixed to one another using welding, adhesive, etc. The stent assembly 10 may then be placed on a catheter and delivered to the bifurcation site similar to the manner described above. In some embodiments, when the proximal stent 20 and the distal stent 30 are adjacent one another, the flaps 40 and 50 may lie flat against the tubular body portions of segments 20 and 30. In such an unexpanded state one flap may overlay the other. In an expanded state the flaps will extend obliquely from the tubular body portions.

Figure 8:
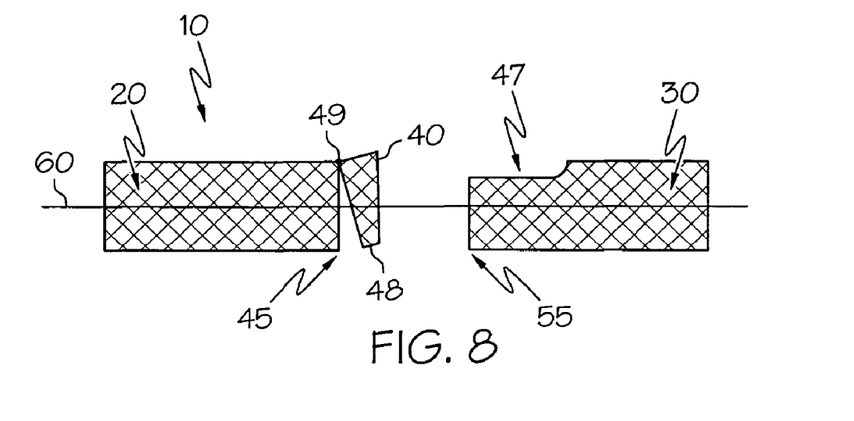
FIG. 8 is a side view of the proximal and distal stents in an unexpanded state.
Figure 9:
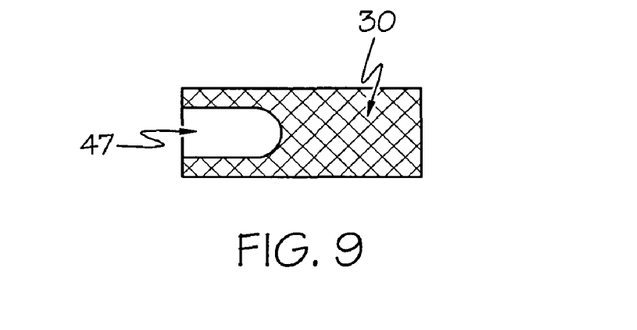
FIG. 9 is a top view of an embodied distal stent.
Figure 10:
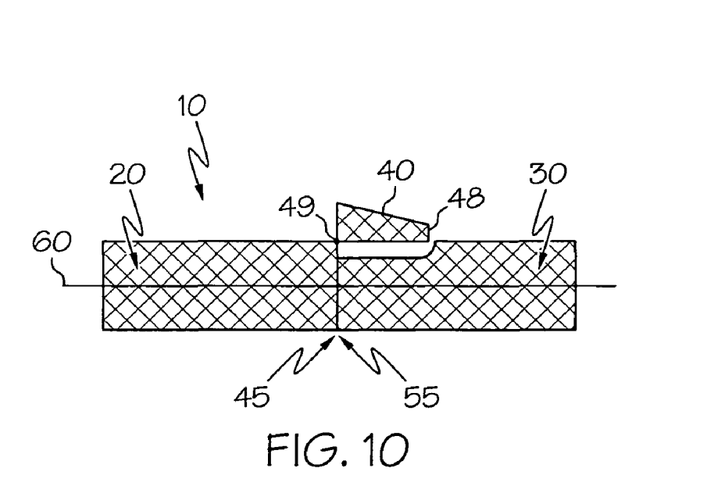
FIG. 10 is a side view of the proximal and distal stents in an expanded state.

In some embodiments the stent assembly 10 has only one flap 40 between the proximal stent 20 and the distal stent 30 as shown in FIGS. 8-10. Though the flap can be on either the proximal stent or the distal stent, as shown it is on the proximal stent 20. A cut-out space 47 allows a space through which the flap 40 can pass through when it is forced to rotate about rotation point 49. Rotation point 49 can either be a point designed with a rotating mechanism or it can merely be the point at which the flap 40 rotates and no mechanism outside of the flexibility of the stent portion is involved. In some embodiments the rotation occurs about a ductile hinge, which may have a cross-sectional area smaller than adjacent portions of the stent and can experience plastic deformation while the rest of a stent does not. The rotation of flap 40 can be through a range of degrees in that expansion can depend in part on the angle between the two lumens at the bifurcation carina. If the angle is smaller at a first carina than at a second carina, then rotation of the flap 40 to the expanded state can be less at the first carina than at the second. In some embodiments the free end 48 of the flap 40 remains within the distal stent 30 and/or the cutout 47.

In the expanded state the flap 40 of the stent assembly 10 illustrated in FIGS. 8-10 can provide support for the contralateral wall and the carina of a bifurcation. In some embodiments, an additional stent or stent graft can extend through the flap 40 to provide extended coverage of the secondary lumen.

Figure 11:
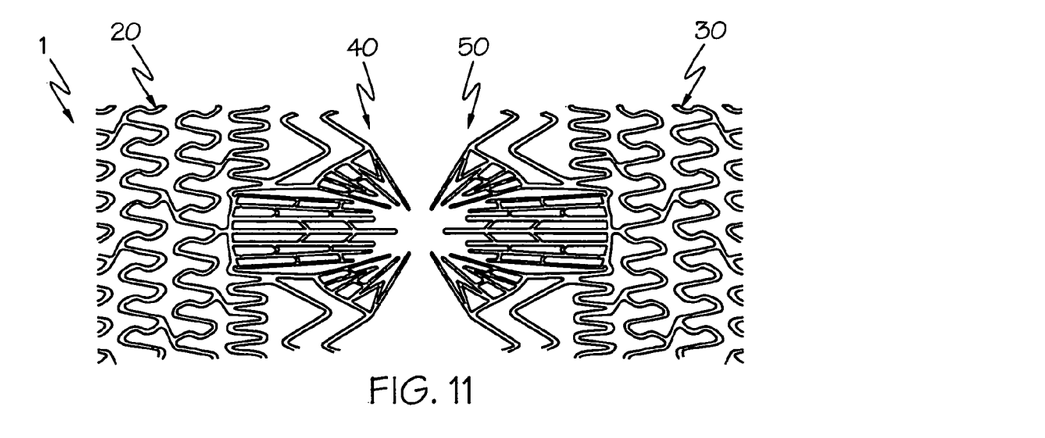
FIG. 11 is a top view of the proximal and distal stents in an unexpanded state when separated.
Figure 12:
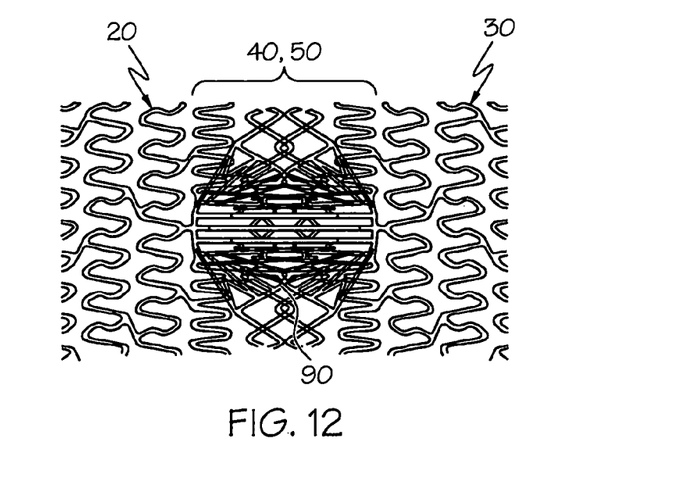
FIG. 12 is a top view of the proximal and distal stents in an unexpanded state wherein the flaps overlap or are nested within one another.

In at least one embodiment an example of which is shown in FIGS. 11-12, the proximal stent 20 and the distal stent 30 are provided with flaps 40 and 50 respectively which overlap one another prior to expansion. This allows the flaps 40,50 to be longer and to provide a greater amount of metal scaffolding than may be present in other types of side branches. In some embodiments the proximal stent 20 and the distal stent 30 are substantially mirror images and the lengths of flaps 40 and 50 can be substantially the same.

Figure 13:
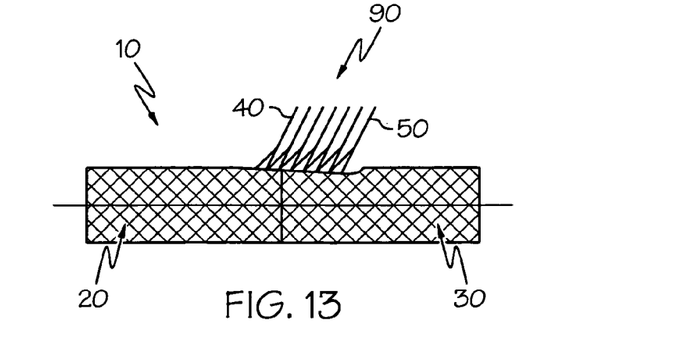
FIG. 13 is a side view of the proximal and distal stents in an expanded state.

The stent assembly 10 is shown expanded in FIG. 13. The flaps 40,50 are expanded and extend to form the side branch 90. More material is available for the flaps 40,50 for vessel coverage as a result of their longer length and overlapping configurations from the adjacent proximal and distal stent. Thus the bifurcated stent assembly 10 is not limited by the material within a single stent. For this reason, the side branch 90 can extend further into the secondary lumen than would a side branch extending from a bifurcated stent cut from a single tube.

The inventive stents may be made from any suitable biocompatible materials including one or more polymers, one or more metals or combinations of polymer(s) and metal(s). Examples of suitable materials include biodegradable materials that are also biocompatible. By biodegradable is meant that a material will undergo breakdown or decomposition into harmless compounds as part of a normal biological process. Suitable biodegradable materials include polylactic acid, polyglycolic acid (PGA), collagen or other connective proteins or natural materials, polycaprolactone, hylauric acid, adhesive proteins, co-polymers of these materials as well as composites and combinations thereof and combinations of other biodegradable polymers. Other polymers that may be used include polyester and polycarbonate copolymers. Examples of suitable metals include, but are not limited to, stainless steel, titanium, tantalum, platinum, tungsten, gold and alloys of any of the above-mentioned metals. Examples of suitable alloys include platinum-iridium alloys, cobalt-chromium alloys including Elgiloy and Phynox, MP35N alloy and nickel-titanium alloys, for example, Nitinol.

The inventive stents may be made of shape memory materials such as superelastic Nitinol or spring steel, or may be made of materials which are plastically deformable. In the case of shape memory materials, the stent may be provided with a memorized shape and then deformed to a reduced diameter shape. The stent may restore itself to its memorized shape upon being heated to a transition temperature and having any restraints removed therefrom.

In some embodiments the stent, the delivery system or other portion of the assembly may include one or more areas, bands, coatings, members, etc. that is (are) detectable by imaging modalities such as X-Ray, MRI, ultrasound, etc. In some embodiments at least a portion of the stent and/or adjacent assembly is at least partially radiopaque.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims may be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the invention. Those skilled in the art may recognize other equivalents to the specific embodiment described herein which equivalents are intended to be encompassed by the claims attached hereto.

What is claimed is:

1. A stent assembly comprising:
a proximal stent and a distal stent, each stent having a tubular body defining a stent lumen, the body further defining a circumference, a proximal flap extending from a distal end of the proximal stent and a distal flap extending from a proximal end of the distal stent, each flap defining only a portion of the circumference, in an expanded state the proximal flap and the distal flap form a side branch support defining a side branch support lumen, the side branch support lumen being in fluid communication with the stent lumen of the proximal stent and distal stent, and having a longitudinal axis different from that of the stent lumen of either the proximal stent and the distal stent.

2. The stent assembly of claim 1 wherein at least a portion of at least one of the proximal stent and distal stent includes at least one therapeutic agent.

3. The stent assembly of claim 2 wherein at least one flap contains a different dosing of therapeutic agent than the tubular body from which the at least one flap extends.

4. The stent assembly of claim 1 wherein at least a portion of the tubular bodies are immediately adjacent one another.

5. The stent assembly of claim 1 wherein a portion of the tubular bodies are engaged to one another.

6. The stent of claim 1 wherein the flaps of the proximal stent segment and the distal stent segment overlap one another.

7. The stent of claim 1 wherein the flaps of the proximal stent segment and the distal stent segment nest within each other.

8. The stent assembly of claim 1 wherein at least one of the first stent and the second stent are at least partially self-expanding from a reduced diameter in an unexpanded state to a greater diameter in the expanded state.

9. The stent assembly of claim 1, wherein at least one of the first stent and the second stent are at least partially balloon expandable from a reduced diameter in an unexpanded state to a greater diameter in the expanded state.

10. A system for delivering a stent assembly to a vessel bifurcation, the system comprising:
a catheter, the catheter having a catheter shaft, a region of the catheter shaft comprising a stent assembly retaining region;
a stent assembly, the stent assembly comprising a proximal stent and a distal stent and being expandable from an unexpanded state to an expanded state, in the unexpanded state the stent assembly being disposed about at least a portion of the stent assembly retaining region, the stent assembly having a tubular body which defines a primary lumen therethrough, both the proximal stent and the distal stent having a flap extending therefrom, each flap comprising a non-tubular body having a substantially planar structure, in the expanded state the flaps form a side branch support defining a side branch support lumen, the side branch support lumen in fluid communication with the primary lumen and having a longitudinal axis different from that of the primary lumen.

11. The system of claim 10 further comprising:
a side branch support guide housing, the side branch support guide housing comprising a tubular member defining a secondary guidewire lumen therethrough, the side branch support guide housing positioned adjacent to the stent assembly retaining region of the catheter shaft, a first portion of the guide housing extending within and through the primary lumen defined by the proximal stent.

12. The system of claim 11, wherein in the expanded state the proximal flap and the distal flap define a space therebetween.

13. The system of claim 12, wherein the distal stent is distal to the side branch support guide housing.

14. The system of claim 13, wherein the catheter shaft defines a first guidewire lumen therethrough.

15. The system of claim 10 wherein the side branch support lumen is substantially oval-shaped.

16. A method of assembling a stent comprising the steps of:
providing a proximal stent and a distal stent, each stent having a tubular body defining a stent lumen, the body further defining a circumference, a proximal flap extending from a distal end of the proximal stent and a distal flap extending from a proximal end of the distal stent;
positioning the distal end of the proximal stent and the proximal end of the distal stent immediately adjacent one another, such that the proximal flap and the distal flap form a side branch support, the side branch support defining a side branch support lumen, the side branch support lumen in fluid communication with the stent lumen of each stent and having a longitudinal axis different from that of the stent lumen of either the proximal stent or the distal stent.

17. The method of claim 16 further comprising the step of welding at least a portion of the distal end of the proximal stent to at least a portion of the proximal end of the distal stent.

18. The method of claim 16 further comprising the step of disposing the proximal stent and the distal stent about a catheter.

19. A method of delivering a stent to a bifurcation site comprising the steps of:
providing a stent delivery system, the stent delivery system comprising:
a catheter, the catheter having a catheter shaft, the catheter shaft defining a first guidewire lumen constructed and arranged to permit sliding passage of a first guidewire therethrough, a region of the catheter shaft comprising a stent assembly retaining region,
a stent assembly, the stent assembly comprising a proximal stent and a distal stent and being expandable from an unexpanded state to an expanded state, in the unexpanded state the stent assembly being disposed about at least a portion of the stent assembly retaining region, the stent assembly having a tubular body which defines a primary lumen therethrough, both the proximal stent and the distal stent each having a flap extending therefrom, each flap comprising a non-tubular body having a substantially planar structure, in the expanded state the flaps form a side branch support defining a side branch support lumen, the side branch support lumen in fluid communication with the primary lumen and having a longitudinal axis different from that of the primary lumen, and a side branch support guide housing, the side branch support guide housing comprising a tubular member defining a secondary guidewire lumen constructed and arranged to permit sliding passage of a second guidewire therethrough, the side branch support guide housing positioned adjacent to the stent assembly retaining region of the catheter shaft, a first portion of the guide housing extending within and through the primary lumen defined by the proximal stent;

advancing the stent delivery system simultaneously along the first guidewire and the second guidewire to a bifurcation of vessels; and deploying the stent assembly at the bifurcation, such that the proximal stent is deployed substantially proximal of the bifurcation, the distal stent is deployed substantially distal of the bifurcation and the side branch support is deployed into a side branch support vessel of the bifurcation.

20. The method of claim 19 wherein the stent assembly retaining region comprises a balloon, the step of deploying the stent assembly including expanding the balloon from a reduced diameter in a pre-deployment configuration to a greater diameter in a deployed configuration.

* * * * *